United States Patent [19]  
Bolton et al.

[11] Patent Number: 4,814,179  
[45] Date of Patent: Mar. 21, 1989

[54] FLOATING SUSTAINED RELEASE THERAPEUTIC COMPOSITIONS

[75] Inventors: Sanford Bolton, Cresskill; Subhash Desai, Plainsboro, both of N.J.

[73] Assignee: St. John's University, New York, N.Y.

[21] Appl. No.: 26,640

[22] Filed: Mar. 17, 1987

Related U.S. Application Data

[63] Continuation-in-part of Ser. No. 722,832, Apr. 12, 1985, abandoned.

[51] Int. Cl.⁴ .................. A61K 9/44; A61K 9/20; A61K 9/22
[52] U.S. Cl. ........................ 424/467; 424/464; 424/468; 424/469; 424/484; 424/455
[58] Field of Search ............... 424/464, 467, 468, 469, 424/484, 488

[56] References Cited

U.S. PATENT DOCUMENTS

| 3,323,922 | 6/1967 | Durst | 106/136 |
| 3,483,002 | 12/1969 | Stein | 426/576 |
| 4,089,981 | 5/1978 | Richardson | 426/576 |
| 4,126,672 | 11/1978 | Sheth | 424/22 |
| 4,140,755 | 2/1979 | Sheth | 424/21 |
| 4,167,558 | 9/1979 | Sheth | 424/22 |
| 4,434,153 | 2/1984 | Urquahart | 424/22 |
| 4,451,260 | 5/1984 | Mitra | 424/890 |
| 4,620,982 | 11/1986 | Sorpelloni | 426/576 |
| 4,690,822 | 9/1987 | Vemura et al. | 424/458 |
| 4,695,467 | 9/1987 | Vemura et al. | 424/475 |
| 4,702,918 | 10/1987 | Ushimara et al. | 514/560 |

OTHER PUBLICATIONS

M. Nakano, Y. Nakamura, K. Takikawa, M. Kouketsu and T. Arita, J. Pharm. Pharmacol., 31, pp. 869–872 (1979).

M. Nakano, K. Takikawa, K. Juni and T. Arita, Chem. Pharm. Bull., 27, pp. 2834–2837 (1979).

M. Nakano, M. Kouketsu, Y. Nakamura and K. Juni, Chem. Pharm. Bull., 28, pp. 2905–2908 (1980).

N. A. Boraie and V. F. Naggar, Acta Pharm. Jugosl., 34, pp. 247–256 (1984).

Primary Examiner—Shep K. Rose  
Attorney, Agent, or Firm—Wyatt, Gerber, Burke & Badie

[57] ABSTRACT

Non-compressed sustained release tablets which will float on gastric fluid are described. The tablets comprise a hydrocolloid gelling agent, a therapeutically acceptable inert oil, the selected therapeutic agent and water.

7 Claims, No Drawings

FLOATING SUSTAINED RELEASE THERAPEUTIC COMPOSITIONS

This is a continuation-in-part of Ser. No. 722,832 filed Apr. 12, 1985, abandoned.

BACKGROUND OF THE INVENTION

1. Field of Invention

This invention relates to therapeutic compositions in unit dosage form which are capable of floating on gastric fluid and delivering their contained therapeutic agent over an extended period of time.

2. Description of the Prior Art

The convenience of administering a single dose of a medication which releases active ingredients over an extended period of time as opposed to the administration of a number of single doses at regular intervals has long been recognized in the pharmaceutical arts. The advantage to the patient and clinician in having consistent and uniform blood levels of medication over an extended period of time are likewise recognized.

The conventional approaches to sustained release can be disadvantageous when the medicament is administered orally because certain classes of active ingredients are not suited to absorption during passage through the gastrointestinal tract due to their physiochemical properties and/or favorable sites of absorption. Penicillin, for example, is fully absorbed at one point in the intestine. Once the dosage unit containing penicillin passes this point under the influence of peristaltic movement, the remaining penicillin is not absorbed into the blood stream, but is excreted.

Most medicaments will undergo varying degrees of change in solubility by passage from the strongly acid conditions of the stomach to the neutral and to the alkaline conditions of the intestines. Additionally, there are medicaments, e.g. antacids which are intended to act in the stomach and therefore lose most beneficial properties when they pass into the intestine.

The advantages of sustained release dosage forms, which are retained in the stomach, for example, by floating in the gastric fluid, slowly releasing their therapeutic contents into the gastric fluid for passage through the intestinal tract, will be readily apparent. These include (1) increased contact time for local activity in the stomach, where such is required, as in the treatment of stomach ulcers, (2) increased and more efficient absorption for drugs which have specific absorption sites, and (3) the ability to reduce the number of dosages.

A number of patents disclose therapeutic dosage forms which float on the gastric fluid and have sustained release capabilities. In a series of U.S. Patents (U.S. Pat. Nos. 4,126,672; 4,140,755; 4,167,558), Sheth and Tossounian claim compressed tablets and capsules containing from about 20% to about 75% by weight of one or a mixture of hydrocolloids as carriers for therapeutic agents. The hydrocolloids recited in the examples and in the claims are cellulose derivatives including methylcellulose, hydroxyalkylcelluloses and carboxymethylcellulose. The products are said to be in hydrodynamic balance so that, upon contact with gastric fluid, the hydrocolloids hydrate and acquire a bulk density of less than one, thereby being buoyant in the gastric fluid. The presence of pharmaceutically inert fatty materials having a specific gravity of less than one decreases the hydrophilicity and increases the buoyancy of the dosage form.

Urquhart and Theeuwes in U.S. Pat. No. 4,434,153 describe a prolonged release system in which coated tiny pills comprising a wall of "drug release rate controlling" wax surrounding a core of medicament, are dispersed in a hydrophilic matrix and compressed to a tablet in which the matrix swells in stomach fluid for extended residency therein.

Mitra in U.S. Pat. No. 4,451,260 describes a sustained release device which is a multilayer composite comprising a carrier film which is water-insoluble and contains a medicament and a barrier film comprising a water-insoluble, water- and medicament-permeable polymer. The two films are sealed in such a way as to entrap a plurality of small pockets of air between said films. The air-containing composite has a bulk density of less than one so as to render it buoyant in gastric fluid. The composite film is cut into desired lengths which are folded to fit inside a gelatin capsule. Upon oral administration, the capsule dissolves and the insoluble composite film floats on the gastric fluid.

Hydrophilic polymers or hydrocolloids have been used in sustained release dosage forms which have been prepared without compression.

The procedure disclosed by Nakano et al in J. Pharm. Pharmacol., 31, 869 (1979) and referred to in Chem. Pharm. Bull., 28, 2905 (1980), involves dissolving agar in water at 90° C. and, after the solution is cooled to 70° C., sulphamethizole is suspended in the agar solution. The drug suspension, containing about 6% agar and 8% drug is then extruded through a plastic syringe onto the top of a cold water-immiscible organic solvent such as ethyl acetate, to form drug-containing beads which are separated from the solvent by filtration and dried. The dried beads contain about 40% agar. There is no indication of the density of the beads or whether they can float on gastric fluid.

A procedure disclosed by Nakano et al in Chem. Pharm. Bull., 27, 2834 (1979) involves swelling konjac flour with water and extruding the resulting sol, containing 5% konjac, from a plastic syringe into boiling water saturated with calcium hydroxide. After a period of boiling, an elastic gel is obtained and is washed with water to remove the alkali. The gel is then placed at 70° C. into an ammoniacal solution containing 5% theophylline to permit the drug to permeate into the gel. The gel containing theophylline is then dried to constant weight and cut into pieces. The dried gel contains 55% konjac. There is no indication of the density of the dried gel or whether the pieces can float on gastric fluid.

Boraie and Naggar in Acta Pharm. Jugosl., 34, 247 (1984) disclose a procedure for preparing non-compressed tablets which involves preparing an aqueous suspension containing at least 7.5% agar and a medicament such as theophylline, at an agar/drug ratio of 1/0.5 to 1/1.33, and charging said suspension into a tablet mold and cooling. The molded tablets are removed from the mold and dried. The dried tablets have an agar content of at least 43%. There is no indication of the density of the dried tablets or whether they will float on gastric fluid.

It is noteworthy that, although Sheth and Tossounian (op cit) disclose the preparation of compressed tablets and capsules which float on gastric fluid, the specifically caution against the use of water or other solvent for the hydrocolloid. "In the practice of the invention, the hydrocolloid is incorporated into the formulation in dry form.... Wherein a hydrocolloid such as described herein is combined in the formulation in the presence of a solvent, such hydrocolloid does not function to facilitate the buoyancy of the tablets prepared therefrom" (U.S. Pat. No. 4,167,558, col. 5, lines 37-53).

The present invention is directed toward a non-compressed therapeutic composition in unit dosage form, having a low concentration of gelling agent and capable of floating on gastric fluid and delivering the therapeutic agent over an extended period of time.

SUMMARY OF THE INVENTION

An object of the present invention is to provide a solid unit dosage form capable of floating on gastric fluid and delivering a therapeutic agent incorporated therein over an extended period of time.

Another object of the present invention is to provide a therapeutic solid unit dosage form as a non-compressed tablet which has a bulk density of less than one and sufficient mechanical stability for production and handling.

It has now been found that these improvements in a therapeutic solid unit dosage form can be achieved by incorporating into the non-compressed tablet, in addition to the therapeutic agent, 0.5 to 4% gelling agent, 10-20% inert oil and water.

DETAILED DESCRIPTION OF THE INVENTION

According to the present invention, therapeutic dosage forms have now been discovered which are easy to prepare, provide sustained release of contained therapeutic agents and float on gastric fluid. These unit dosage forms, which are in the form of tablets, although not compressed, have sufficient mechanical stability and hardness so that they will withstand the normal stress of production, packaging and dispensing. They have a density which is less than one and sufficiently low so that they will float on gastric fluid. Typically, the density is from about 0.6 to 0.95.

The tablets contain as essential ingredients, the therapeutic agent in sufficient concentration to be therapeutically effective, about 0.5 to 4% of a gelling agent, 10-20% of a therapeutically acceptable inert oil and water.

The optimum concentration of the therapeutic agent in the non-compressed tablet will, of course, vary with the identity of the therapeutic agent and its optimum therapeutic dosage. Generally, the amount of the agent in the tablet will be from about 50 to about 75% by weight based on the total weight of the tablet. (All percentages by weight in this disclosure and claims are based on total weight.)

Except for those which must be protected from the gastric fluid, there is practically no limitation to the therapeutic agents which can be administered in accordance with this invention. They include, for example, analgesics, anorexias, antacids, antibiotics, antidiabetics, antihistamines, steroids, antinauseants, antispasmodies, cardiovascular preparations, decongestants, diuretics, geriatrics, muscle relaxants, tranquilizers and vitamins. More specific examples include theophylline, acetaminophen, ampicillin, atropine, penicillin, tetracycline, chlorathiazide, phenytoin, riboflavin, quinidine, cimetidine, captopril, indomethicin, prednisolone and estradiol. The agents can be employed as free bases or as metal or acid addition salts.

The gelling agents which may be used in the present invention are hydrocolloids, i.e. materials capable of absorbing aqueous fluids and undergoing swelling. The effective hydrocolloids are well known in the art and include natural products such as agar, agarose, carrageenan, konjac gum, locust bean gum, alginic acid and its salts, starch and the like, as well as modified natural products such as certain water-swellable cellulose derivatives and synthetic products such as polyacrylic acid and the like. The concentration of gelling agent in the non-compressed tablet is about 0.5 to 4% by weight of the total weight of the tablet. Mixtures of gelling agents may be employed.

The low concentrations of gelling agents which are effective in the tablets of this invention are unexpected in view of the significantly higher concentrations disclosed in the prior art in both compressed and non-compressed tablets as well as capsules, gels and beads.

The therapeutically acceptable inert oils which may be used in the present invention include mineral oils, vegetable oils and other hydrocarbon oils which generally have a density below one. Inert waxes may also be used. The term "inert" refers to chemically inert, i.e. no reaction with any of the components of the tablet.

The concentration of inert oil in the non-compressed tablet is from 10 to 20%. The preferred concentration is from 12 to 20% of the total weight of the tablet.

The tablet may also contain other conventional additives and excipients such as thickening agents, surfactants, preservatives, bulking agents and antioxidants.

The tablets of this invention have a density of less than one and will float on gastric fluid in vivo. They are sustained release dosage units, i.e. they release their medicaments over an extended period of time. The actual rate of release varies with the amount of exposed surface area and, therefore, with size and shape of the tablet.

The non-compressed tablets of the present invention may be prepared by the following method:

1. Prepare a solution of the hydrocolloid gelling agent and excipients, if any, in hot water;
2. Prepare a mixture of a therapeutic agent and a therapeutically acceptable inert oil;
3. Cool the solution of gelling agent, but not to the point where gelation takes place, and combine the solution and the mixture from step (2) with stirring, while maintaining the temperature above the gelation temperature;
4. Pour the mixture from step (3) into a tablet mold and allow to stand in the mold to form a gel; and
5. Dry the molded gel tablets to reduce the water content.

The solution temperature for the gelling agent is generally about 70° to 100° C. and the pour temperature of the mixture is about 50° to 70° C. The specific temperature depends upon the gelling agent used in the formulation.

Variations of this procedure will be readily apparent to those skilled in the art.

The concentration of the various components in the aqueous mixture is 0.5 to 2% gelling agent, 5 to 30% therapeutically acceptable inert oil, 25 to 50% therapeutic agent and the balance is water. The exact amount of therapeutic agent may vary appreciably depending upon the effective therapeutic dosage.

During the gelation and drying steps, most of the water evaporates. The resulting product, although it is not compressed, is a hard tablet in the shape of the mold. Its hardness and compression strength, as well as friability, are comparable to those of most commercially available compressed therapeutic tablets. It is characterized by a network of multitudinous air holes and passages. It is surprising to find that such small quantities of gelling agents are capable of forming such rugged tablets without compression.

The following examples are given by way of illustration only and are not to be considered limitations of this invention, many apparent variations of which are possible without departing from the spirit or scope thereof.

EXAMPLE 1

Theophylline tablets were prepared from the following formulation, using agar as gelling agent:

| Ingredients | grams | % |
|---|---|---|
| Theophylline | 9.0 | 42.4 |
| Light mineral oil | 2.0 | 9.4 |
| Agar | 0.2 | 0.9 |
| Water | 10.0 | 47.2 |

The theophylline and mineral oil were charged into a beaker and stirred. Water and agar were placed in a separate beaker, stirred and heated to boiling to effect solution. The agar solution was cooled to 70° C. and gradually added to the theophylline-oil mixture with vigorous stirring to form an oil-in-water emulsion. The warm emulsion was poured at 50°-55° C. into a tablet mold in which the cylindrical holes had a height of about 0.46 cm and a diameter of about 1.10 cm. The compositions in the holes were allowed to cool and gelled in about 5 minutes. The tablets were removed from the mold and air dried for 24 hours. The average density of the tablets (average of 10 tablets) was 0.70.

The release of theophylline from the tablets was determined using the U.S. Pharmacopeia basket method at 50 rpm and 37° C. The dissolution medium was either at pH 1.2 (concentrated HCl diluted with distilled water) or pH 7.4 (buffer solution containing sodium hydroxide, potassium phosphate and distilled water, as described in U.S.P. XX).

The floating tablets had the following release pattern:

| Time, hours | pH 1.2 | | pH 7.4 | |
|---|---|---|---|---|
| | % Released | Cumulative % | % Released | Cumulative % |
| 1 | 23.8 | 23.8 | 26.1 | 26.1 |
| 2 | 7.6 | 31.4 | 10.6 | 36.7 |
| 4 | 12.0 | 43.4 | 13.6 | 50.3 |
| 8 | 21.7 | 65.1 | 15.6 | 65.9 |
| 12 | 9.4 | 74.5 | | |
| 13 | | | 14.1 | 80.0 |

EXAMPLE 2

Theophylline tablets were prepared in the same manner as described in Example 1, using agar as gelling agent, in the following formulation:

| Ingredients | grams | % |
|---|---|---|
| Theophylline | 9.0 | 40.5 |
| Light mineral oil | 3.0 | 13.5 |
| Agar | 0.2 | 0.9 |
| Water | 10.0 | 45.0 |

The molded tablets were air dried for 24 hours. The average tablet size was 1.11×0.45 cm, the average tablet weight was 317 mg and the average tablet density was 0.718.

The composition of the dried tablets was determined by extraction and analysis. Thus, 10 tablets were crushed and extracted with n-hexane. The hexane was evaporated at 50° C. to yield the amount of extracted mineral oil. The theophylline content was determined by UV analysis and the water content was determined by Karl Fischer titration of 10 tablets. The amount of agar was determined by difference.

The composition of the dried tablets was as follows:

| Ingredients | mg | % |
|---|---|---|
| Theophylline | 237.0 | 74.8 |
| Light mineral oil | 60.0 | 18.9 |
| Agar | 5.3 | 1.7 |
| Water | 14.7 | 4.6 |

The floating tablets had the following release pattern at 50 rpm and 37° C. in dissolution media of pH 1.2 and 7.4:

| Time, hours | pH 1.2 | | pH 7.4 | |
|---|---|---|---|---|
| | % Released | Cumulative % | % Released | Cumulative % |
| 1 | 21.0 | 21.0 | 20.4 | 20.4 |
| 3 | 17.5 | 38.5 | 17.3 | 37.7 |
| 6 | 16.3 | 54.8 | 15.7 | 53.4 |
| 12 | 21.1 | 75.9 | 21.5 | 74.9 |
| 19 | 15.4 | 91.3 | 16.3 | 91.2 |

Plasma concentrations of theophylline in a human adult male volunteer were determined after ingestion of a single tablet containing 237 mg theophylline.

| Time, hours | Concentration, mcg/ml |
|---|---|
| 1 | 0 |
| 3 | 1.7 |
| 6 | 1.95 |
| 12 | 2.7 |
| 18 | 3.75 |
| 24 | 3.2 |

The sustained release of the medicament is evident from the plasma concentrations.

EXAMPLE 3

Theophylline tablets were prepared as described in Example 1, using agar as the gelling agent, in the following formulation:

| Ingredients | grams | % |
|---|---|---|
| Theophylline | 6.0 | 33.0 |
| Mineral oil | 2.0 | 11.0 |
| Agar | 0.2 | 1.1 |
| Water | 10.0 | 54.9 |

The molded gel tablets were air dried for 24 hours. The size of the dry tablet was 1.11×0.48 cm and the average weight was 231 mg per tablet. The tablet hardness, determined with a Pfizer hardness tester, was 6.1 kg and the average tablet density was 0.560.

The dissolution test was carried out by the basket method at 50 rpm and 37° C. in a 0.1N HCl dissolution medium (pH 1.3). The floating tablets had the following release pattern:

| Time, hours | % Released | Cumulative % |
| --- | --- | --- |
| 1 | 24 | 24 |
| 2 | 11 | 35 |
| 3 | 7 | 42 |
| 4 | 5 | 47 |
| 5 | 4 | 51 |
| 6 | 5 | 56 |
| 8 | 7 | 63 |

EXAMPLE 4

Theophylline tablets were prepared as described in Example 1, using iota carrageenan as the gelling agent, in the following formulation:

| Ingredients | grams | % |
| --- | --- | --- |
| Theophylline | 6.0 | 32.8 |
| Iota carrageenan | 0.3 | 1.6 |
| Mineral oil | 2.0 | 10.9 |
| Water | 10.0 | 54.6 |

After 24 hours air drying, the 1.11×0.48 cm tablet weighed 234 mg, the hardness was 6.2 kg and the density was 0.576.

The dissolution test was conducted in 0.1N HCl (pH 1.3) at 50 rpm at 37° C. The floating tablets had the following release pattern:

| Time, hours | % Released | Cumulative % |
| --- | --- | --- |
| 1 | 25 | 25 |
| 2 | 21 | 46 |
| 3 | 16 | 62 |
| 4 | 10 | 72 |
| 6 | 19 | 91 |

EXAMPLE 5

Theophylline tablets were prepared as described in Example 1, using kappa carrageenan as the gelling agent, in the following formulation:

| Ingredients | grams | % |
| --- | --- | --- |
| Theophylline | 6.0 | 32.8 |
| Kappa carrageenan | 0.3 | 1.6 |
| Mineral oil | 2.0 | 10.9 |
| Water | 10.0 | 54.6 |

After 24 hours air drying, the 1.11×0.48 cm tablet weighed 237 mg, the hardness was 5.2 kg and the density was 0.580.

The dissolution test was conducted in 0.1N HCl (pH 1.3) at 50 rpm and 37° C. the floating tablets had the following release pattern:

| Time, hours | % Released | Cumulative % |
| --- | --- | --- |
| 1 | 40 | 40 |
| 2 | 30 | 70 |
| 3 | 18 | 88 |
| 4 | 5 | 93 |
| 5 | 3 | 96 |

EXAMPLE 6

Theophylline tablets were prepared as described in Example 1, using a mixture of kappa carrageenan and locust bean gum as gelling agent in the following formulation:

| Ingredients | grams | % |
| --- | --- | --- |
| Theophylline | 6.0 | 33.0 |
| Kappa carrageenan | 0.1 | 0.5 |
| Locust bean gum | 0.1 | 0.5 |
| Mineral oil | 2.0 | 11.0 |
| Water | 10.0 | 54.9 |

After 24 hours air drying, the 1.11×0.48 cm tablet weighed 224 mg and the hardness was 5.6 kg. The density of the tablet was 0.562.

The dissolution test was carried out in 0.1N HCl (pH 1.3) at 50 rpm and 37° C. The floating tablets had the following release pattern:

| Time, hours | % Released | Cumulative % |
| --- | --- | --- |
| 1 | 27 | 27 |
| 2 | 21 | 48 |
| 3 | 17 | 65 |
| 4 | 15 | 80 |
| 5 | 7 | 87 |
| 6 | 7 | 94 |

EXAMPLE 7

Theophylline tablets were prepared as described in Example 1, using a mixture of iota carrageenan and locust bean gum as gelling agent in the following formulation:

| Ingredients | grams | % |
| --- | --- | --- |
| Theophylline | 6.0 | 32.8 |
| Iota carrageenan | 0.2 | 1.1 |
| Locust bean gum | 0.1 | 0.5 |
| Mineral oil | 2.0 | 10.9 |
| Water | 10.0 | 54.6 |

After 24 hours air drying, the 1.11×0.48 cm tablet weighed 221 mg, the hardness was 7.9 kg and the density was 0.546.

The dissolution test was conducted in 0.1N HCl (pH 1.3) at 50 rpm and 37° C. The floating tablets had the following release pattern:

| Time, hours | % Released | Cumulative % |
| --- | --- | --- |
| 1 | 20 | 20 |
| 2 | 11 | 31 |
| 3 | 8 | 39 |
| 4 | 6 | 45 |
| 5 | 6 | 51 |
| 6 | 6 | 57 |
| 8 | 5 | 63 |
| 10 | 10 | 73 |

| Time, hours | % Released | Cumulative % |
|---|---|---|
| 12 | 6 | 79 |

EXAMPLE 8

Theophylline tablets were prepared as described in Example 1, using a mixture of alginic acid and locust bean gum as gelling agent, in the following formulation:

| Ingredients | grams | % |
|---|---|---|
| Theophylline | 6.0 | 32.8 |
| Alginic acid | 0.2 | 1.1 |
| Locust bean gum | 0.1 | 0.5 |
| Mineral oil | 2.0 | 10.9 |
| Water | 10.0 | 54.6 |

After 24 hours air drying, the 1.11=0.48 cm tablet weighed 226 mg and the hardness was 7.4 kg. The density of the tablet was 0.554.

The dissolution test was conducted in 0.1N HCl (pH 1.3) at 50 rpm and 37° C. The floating tablets had the following release pattern:

| Time, hours | % Released | Cumulative % |
|---|---|---|
| 1 | 20.2 | 20.2 |
| 2 | 7.7 | 27.9 |
| 3 | 6.8 | 34.7 |
| 4 | 4.4 | 39.1 |
| 5 | 4.7 | 43.8 |
| 6 | 4.1 | 47.9 |
| 8 | 6.2 | 54.1 |
| 10 | 5.5 | 59.6 |
| 12 | 5.0 | 64.6 |

EXAMPLE 9

Ampicillin floating tablets were prepared using agar as the gelling agent, according to the following formulation:

| Ingredients | grams | % |
|---|---|---|
| Ampicillin, anhydrous | 90.0 | 32.5 |
| Light mineral oil | 16.0 | 5.8 |
| Agar | 3.2 | 1.15 |
| Sodium citrate | 8.0 | 2.9 |
| Water | 160.0 | 57.7 |

This formulation was used to make a batch of 300 tablets. The mineral oil was added to the ampicillin previously charged into a 500 ml beaker and mixed thoroughly with a glass rod. In a separate beaker, the water was heated to 90° C. and the sodium citrate was dissolved therein with stirring. The agar was added to the aqueous solution and stirred while heating until the agar dissolved. The ampicillin-oil mixture which was in the form of a powder was added in portions to the agar solution at 70° C. and mixed with an electric whisk until a smooth, creamy suspension was obtained. The suspension was poured into a tablet mold at 48°-50° C. The suspension gelled after cooling for 10 minutes. The excess was scraped off the top of the molds, the tablets were pushed out of the molds and air dried at room temperature for 24 hours.

The average weight of the 1.11×0.635 cm tablets was 423 mg and the density was 0.69. The hardness was 11.7 kg and the friability was 0.9%. The dissolution test was carried out in water at 100 rpm and 37° C. The floating tablets had the following release pattern:

| Time, hours | % Released | Cumulative % |
|---|---|---|
| 1 | 17.8 | 17.8 |
| 2 | 9.9 | 27.7 |
| 3 | 7.0 | 34.7 |
| 4 | 5.8 | 40.5 |
| 5 | 4.4 | 44.9 |
| 6 | 4.7 | 49.6 |
| 7 | 3.1 | 52.7 |
| 8 | 2.6 | 55.3 |
| 10 | 5.1 | 60.4 |
| 12 | 3.2 | 63.6 |
| 14 | 5.5 | 69.1 |
| 16 | 3.4 | 72.5 |
| 18 | 4.6 | 77.1 |

EXAMPLE 10

Ampicillin floating tablets were prepared by the following formulation using agar as the gelling agent:

| Ingredients | grams | % |
|---|---|---|
| Ampicillin, anhydrous | 6.0 | 32.1 |
| Light mineral oil | 2.0 | 10.7 |
| Agar | 0.2 | 1.1 |
| Sodium citrate | 0.5 | 2.7 |
| Water | 10.0 | 53.5 |

The tablets were prepared in the same manner as described in Example 9. The dissolution test on the air dried tablets was conducted in water at 50 rpm and 37° C. The floating tablets had the following release pattern:

| Time, hours | % Released | Cumulative % |
|---|---|---|
| 2 | 16.9 | 16.9 |
| 4 | 10.8 | 27.7 |
| 6 | 10.0 | 36.7 |
| 8 | 6.6 | 43.3 |
| 10 | 4.9 | 48.2 |
| 12 | 6.0 | 54.2 |

EXAMPLE 11

Captopril tablets were prepared in the same manner as described in Example 9, using agar as gelling agent, according to the following recipe:

| Ingredients | grams | % |
|---|---|---|
| Captopril | 7.0 | 35.7 |
| Light mineral oil | 1.0 | 5.1 |
| Agar | 0.3 | 1.5 |
| Lactose | 1.0 | 5.1 |
| Calcium gluconate | 0.3 | 1.5 |
| Water | 10.0 | 51.0 |

The captopril-oil mixture was added to the aqueous solution containing agar, lactose and calcium gluconate at 70° C. and after mixing thoroughly was poured into the tablet mold at 50° C. The molded gel tablets were air dried for 36 hours. The size of the dried tablet was 0.95×0.32 cm and the average tablet weight was 134 mg. The hardness was 9.9 kg and the average tablet density was 0.817. A friability test showed a loss of 0.84%.

The dissolution test was carried out by the U.S.P. basket method at 50 rpm and 37° C. using a dissolution medium containing 0.1N HCl and 0.001% ethylenediaminetetraacetic acid. The floating tablets showed the following release pattern:

| Time, hours | % Released | Cumulative % |
| --- | --- | --- |
| 1 | 63.7 | 63.7 |
| 2 | 24.2 | 87.9 |
| 3 | 7.2 | 95.1 |
| 4 | 4.6 | 99.7 |

EXAMPLE 12

Captopril tablets were prepared in the same manner as described in Example 9, using agar as gelling agent, in the following formulation:

| Ingredients | grams | % |
| --- | --- | --- |
| Captopril | 7.0 | 36.3 |
| Light mineral oil | 2.0 | 10.4 |
| Agar | 0.3 | 1.5 |
| Water | 10.0 | 51.8 |

The molded gel tablets were air dried for 24 hours. The size of the dried tablets was 0.95×0.32 cm and the average weight was 125 mg per tablet. The tablet hardness was 6.2 kg and the tablet density averaged 0.690.

The foregoing is exemplary and illustrative of compositions and products responding to the present invention, but it is to be understood that they are not limitative since many active medicaments of various types, many different gelling agents and many different oils can be employed in the new non-compressed tablets.

What is claimed is:

1. A therapeutic composition in unit dosage form as a non-compressed tablet having a network of multitudinous air holes and passages therein and a density of less than one and capable of floating on gastric fluid in vivo and providing sustained release of the therapeutic agent over an extended period of time, comprising a matrix formed from a gelling agent containing a therapeutic agent, a therapeutically acceptable inert oil and water in the following percentages by weight based on the total weight of the tablet: gelling agent, 0.5 to 4%; oil, 10 to 20%; therapeutic agent, 50 to 75%; balance water.

2. The composition according to claim 1 in which the gelling agent is one or more agents selected from the group consisting of agar, carrageenan, locust bean gum and alginic acid.

3. A therapeutic composition in unit dosage form as a non-compressed tablet having a network of multitudinous air holes and passages therein and a density of less than one and capable of floating on gastric fluid in vivo and providing sustained release of the therapeutic agent over an extended period of time, comprising a matrix formed from a gelling agent containing theophylline, a therapeutically acceptable inert oil and water in the following percentages by weight based on the total weight of the tablet: gelling agent, 0.5 to 4%; oil, 10 to 20%; theophylline, 50 to 75%; balance water.

4. The composition according to claim 3 in which the gelling agent is one or more agents selected from the group consisting of agar, carrageenan, locust bean gum and alginic acid.

5. A method of forming a non-compressed tablet having a network of multitudinous air holes and passages therein, and a density of less than one and capable of floating on gastric fluid in vivo and providing sustained release of the therapeutic agent over an extended period of time, which comprises:
  (1) forming a solution of gelling agent in water,
  (2) forming a first mixture containing a therapeutic agent and a therapeutically acceptable inert oil,
  (3) cooling said solution, but not to the point where gelation takes place,
  (4) combining the solution and the first mixture to produce a second mixture containing from 0.5 to 2% of the gelling agent, 5 to 30% of the oil, 25 to 50% of the therapeutic agent and the balance water, all by weight based on the total weight,
  (5) pouring the second mixture into a tablet mold and letting it stand in the mold to form a gel, and
  (6) drying the molded gel tablets to reduce the water content.

6. A method according to claim 5 in which the gelling agent is one or more agents selected from the group consisting of agar, carrageenan, locust bean gum and alginic acid.

7. A method according to claim 5 in which the therapeutic agent is theophylline.

* * * * *